(12) United States Patent
Finke et al.

(10) Patent No.: US 9,675,534 B2
(45) Date of Patent: Jun. 13, 2017

(54) PREPARATIONS WITH IMPROVED PHYSICAL PROPERTIES

(71) Applicant: SYMRISE AG, Holzminden (DE)

(72) Inventors: Anja Finke, Holzminden (DE); Sabine Lange, Holzminden (DE); Gerhard Schmaus, Höxter-Bosseborn (DE)

(73) Assignee: SYMRISE AG, Holzminden (DE)

( * ) Notice: Subject to any disclaimer, the term of this patent is extended or adjusted under 35 U.S.C. 154(b) by 47 days.

(21) Appl. No.: 14/638,367

(22) Filed: Mar. 4, 2015

(65) Prior Publication Data

US 2015/0250693 A1 Sep. 10, 2015

(30) Foreign Application Priority Data

Mar. 7, 2014 (EP) .................................. 14158336

(51) Int. Cl.
*A61K 8/06* (2006.01)
*A61K 8/34* (2006.01)
(Continued)

(52) U.S. Cl.
CPC .............. *A61K 8/37* (2013.01); *A61K 8/062* (2013.01); *A61K 8/34* (2013.01); *A61Q 5/02* (2013.01);
(Continued)

(58) Field of Classification Search
CPC . A61K 8/06; A61K 8/062; A61K 8/34; A61K 8/37; A61K 2800/52; A61Q 5/02; A61Q 19/10; B01F 17/0021
See application file for complete search history.

(56) References Cited

U.S. PATENT DOCUMENTS 8,513,180 B2 * 8/2013 Wiedemann ........... A61K 8/068
512/1
2003/0007986 A1 1/2003 Stora et al.
(Continued)

FOREIGN PATENT DOCUMENTS

EP 2316408 A1 5/2011

OTHER PUBLICATIONS

Extended European Search Report from the parallel European Patent Application No. 14158336.9, received on Sep. 18, 2014.

*Primary Examiner* — Brian P Mruk
(74) *Attorney, Agent, or Firm* — Polsinelli PC

(57) ABSTRACT

The present disclosure relates to a surfactant-containing preparation comprising one or more alcohols and one or more anionic surfactants, wherein the preparation is an O/W emulsion, the particle size distribution for which the following applies: D(v, 0.9)=40 μm or less, and wherein the total quantity of the one or more alcohols in the preparation is selected in such a way that the preparation, compared to a comparison preparation which having an otherwise identical composition does not comprise any alcohol of the formula (I), has an increased viscosity at 22.7 ° C. Also disclosed are methods for producing the preparation and methods for increasing stability and/or viscosity of an emulsion.

18 Claims, 5 Drawing Sheets

(51) Int. Cl.
　　*A61K 8/37*　　　(2006.01)
　　*A61Q 5/02*　　　(2006.01)
　　*A61Q 19/10*　　(2006.01)
　　*B01F 17/00*　　(2006.01)

(52) U.S. Cl.
　　CPC .......... *A61Q 19/10* (2013.01); *B01F 17/0021* (2013.01); *A61K 2800/52* (2013.01)

(56) References Cited

U.S. PATENT DOCUMENTS

2009/0238787  A1　　9/2009　Finke et al.
2012/0101020  A1*　4/2012　Wiedemann ........... A61K 8/068
　　　　　　　　　　　　　　　　　　　　　512/1

* cited by examiner

PREPARATIONS WITH IMPROVED PHYSICAL PROPERTIES

CROSS-REFERENCE TO RELATED APPLICATION

This application claims benefit of priority to European application 14158336.9-1357, filed Mar. 7, 2014, which is incorporated herein by reference in its entirety.

The present invention relates to a preparation with improved physical properties.

If the preparation according to the invention is an O/W emulsion (oil-in-water emulsion, i.e. oil droplets in water) then it has a particle size distribution for which the following applies: D(v, 0.9)=40 µm or less. Preferably, the droplet size lies in a range up to 40 µm, preferably in a range up to 30 µm. The preparation, as a result of the presence of one or more alcohols of the formula (I)

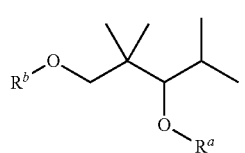

(I)

(see further below for the meaning of the substituents $R^b$ und $R^a$), is set in such a way that the O/W emulsion, compared to a comparison emulsion which having an otherwise identical composition does not comprise any alcohol of the formula (I), has an increased emulsion stability.

If the preparation according to the invention is a (preferably single-phase) surfactant-containing preparation, the total quantity of one or more alcohols of the formula (I) (again, see further below for the meaning of the substituents $R^b$ und $R^a$) in the preparation is selected in such a way that the surfactant-containing preparation, compared to a comparison preparation which having an otherwise identical composition does not comprise any alcohol of the formula (I), has an increased viscosity at 22.7° C.

The preparation according to the invention can be a surfactant-containing O/W emulsion. If it is such a surfactant-containing O/W emulsion, as a result of the stated presence of alcohols of the formula (I) as specified, the emulsion stability is increased and/or the viscosity is increased.

The present invention additionally relates to an O/W emulsion comprising as the emulsifying agent one or more alcohols of the above formula (I), having a particle size distribution for which the following applies:

D(v, 0.9)=40 µm or less, preferably D(v, 0.9)=30 µm or less,

D(v, 0.5)=20 µm or less, preferably D(v, 0.5)<[sic=? as in claim 6] 15 µm or less.

The present invention additionally relates to an O/W emulsion comprising as the emulsifying agent one or more alcohols of the above formula (I), wherein the stability of the emulsion is set in such a way that after storing this emulsion for 3 weeks (21 days) at 25° C. and at a pressure of 1013 HPa hermetically sealed the following applies for the particle size distribution: D(v, 0.9) $(t_{21d})$:D(v, 0.9) $(t_{0d})$<2, preferably <1.5, particularly preferably <1.2 (i.e. the quotient from D(v, 0.9) after 21 days (numerator) und D(v, 0.9) at the starting time of storage (denominator) is <2, preferably <1.5, particularly preferably <1.2).

The present invention additionally relates to a (preferably single-phase) surfactant-containing preparation comprising one or more alcohols of the above formula (I) as the means for increasing the viscosity at 22.7° C. and one or more anionic surfactants, which are preferably selected from the group consisting of sulphates and sulphonates, particularly preferably comprising sodium lauryl ether sulphate and optionally one or more further surfactants.

The invention also relates to the use (a) of a single alcohol of the formula (I) or (b) of a mixture comprising or consisting of two or more different alcohols of the above formula (I) as the means for modifying one or more physical properties of a preparation, wherein the physical properties are selected from the group consisting of emulsion stability and viscosity. Within the scope of the present invention, preparations in particular comprise medical and cosmetic formulations, in particular including body care products (for example cosmetic preparations such as hair dye, hair shaping or depilatory products), and household and (surfactant-containing) cleaning products.

Finally, the present invention also relates to a method for producing and/or stabilising an O/W emulsion, having the following steps:

mixing two (under the given conditions not fully miscible) liquids in the presence of a quantity of one, two or more alcohols of the above formula (I) acting in an emulsifying manner.

Furthermore, the present invention also relates to a method for producing a surfactant-containing preparation with increased viscosity having the following steps:

mixing a surfactant-containing liquid with a quantity of one, two or more alcohols of the above formula (I) which increases the viscosity.

Figure 1:
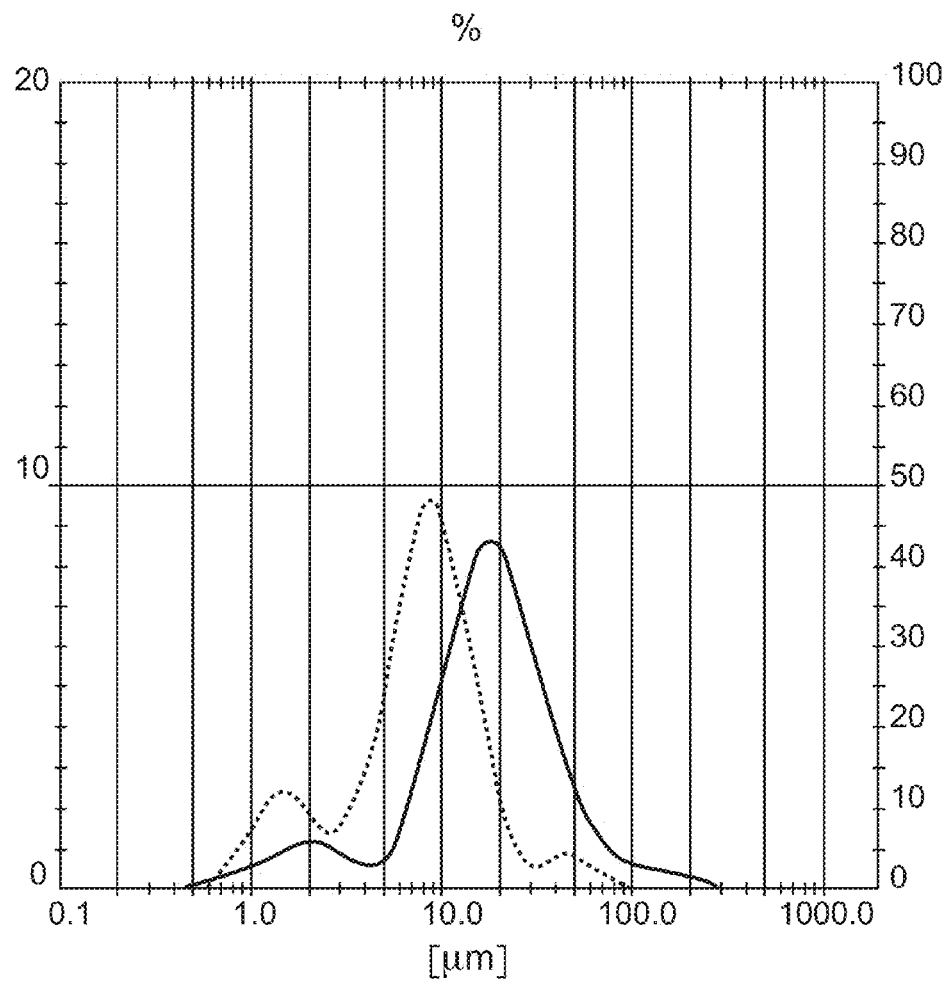
FIG. 1: shows the particle size distribution curve for D(v, 0.5) for samples 1 and 4.

There is a constant requirement for chemical preparations, in particular for cosmetic and medical preparations, whose physical properties are specifically set. Correspondingly there is also a constant requirement for additives which by adding them are capable of modifying base preparations in such a way that the desired physical properties are obtained.

For example, there is a constant requirement for new O/W emulsions and surfactant-containing preparations with customised physical properties. In the case of O/W emulsions, in particular in the case of such O/W emulsions which are provided as cosmetic or medical preparations, often great store is set on these emulsions looking particularly white.

In the area of surfactant-containing preparations, there is often the requirement for these preparations to have a comparably high viscosity, particularly if the preparations concerned are surfactant-containing (cleansing) preparations for cosmetic purposes.

In our own tests relating to O/W emulsions, it was assumed that the degree of whiteness of an O/W emulsion essentially depended on which particle size distribution the emulsified oil particles have within the aqueous continuous phase. Thus, a higher degree of whiteness always results if many of the emulsified particles have a particularly small particle size. Acceptable degrees of whiteness were consistently obtained in our own tests when the following applied for the particle size distribution in the O/W emulsion: D(v, 0.9)=40 μm or less, preferably 30 μm or less. Preferably, the droplet size lies in a range up to 40 μm, preferably in a range up to 30 μm. It goes without saying here that when creating and developing a new O/W emulsion, it does not just come down to uniquely or just primarily setting a particle size distribution for the emulsified particles which provides a high degree of whiteness, but rather, at the same time, to make sure that this particle size distribution is also kept stable over a long storage period.

It was an object of the present invention to specify preparations, namely O/W emulsions and surfactant-containing preparations, whose physical properties are particularly advantageously set. With regard to the O/W emulsions, the aim according to one partial aspect of the present invention was to specify a particularly stable emulsion with a high degree of whiteness. With regard to the surfactant-containing preparations, the aim according to a further partial aspect of the present invention was to obtain a comparably high viscosity at 22.7° C.

It has become apparent in our own tests that the above mentioned object (also with regard to the mentioned partial aspects) can be achieved using the same chemical additives.

According to a first aspect of the present invention, the object set is achieved by a preparation comprising
one or more alcohols of the formula (I)

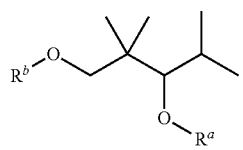

(I)

wherein in each case one of the two moieties $R^a$ or $R^b$ represents hydrogen and the other moiety $R^a$ or $R^b$ in each case represents a straight-chain or branched acyl moiety having 2 to 10 carbon atoms,
and
one or more further compounds,
wherein the preparation is an O/W emulsion, the particle size distribution for which the following applies: D(v, 0.9)=40 μm or less, wherein in the preparation the total quantity of the alcohol(s) of the formula (I) is selected in such a way that the O/W emulsion, compared to a comparison emulsion which having an otherwise identical composition does not comprise any alcohol of the formula (I), has an increased emulsion stability,
and/or
wherein the preparation is a (preferably single-phase) surfactant-containing preparation and the total quantity of the alcohol(s) of the formula (I) in the preparation is selected in such a way that the preparation, compared to a comparison preparation which having an otherwise identical composition does not comprise any alcohol of the formula (I), has an increased viscosity at 22.7° C.

Preferably, D(v, 0.9)=30 μm or less applies for the particle size distribution of the above mentioned O/W emulsions. Particularly preferably, the droplet size (in an O/W emulsion which is otherwise as defined above) lies in a range up to 40 μm, preferably in a range up to 30 μm.

A preparation (as defined above) is particularly preferred, wherein $R^a$ of the one alcohol of the formula (I) represents hydrogen, or wherein $R^a$ (i) of a single alcohol of the formula (I) (from a number of alcohols in total of the formula (I)) or (ii) with two, three or more than three alcohols of this number of alcohols in total of the formula (I) or (iii) with all of this number of alcohols in total of the formula (I) represents hydrogen.

A preparation (as defined above, in particular as defined as preferred above) comprising at least one alcohol of the formula (I) is most particularly preferred, wherein $R^a$ represents hydrogen, preferably $R^a$ represents hydrogen and $R^b$ represents a straight-chain or branched acyl moiety having 3 to 6 carbon atoms (the above mentioned and preferred meanings for $R^a$ and $R^b$ apply most particularly preferably for preparations which are O/W emulsions).

Compounds of the above formula (I) have already been disclosed and discussed in the publication EP 2 133 102 A1 with reference to many other documents from the prior art. According to EP 2 133 102 A1, compounds of the formula (I) are outstandingly suitable for reducing odours.

Compounds of the formula (I) are monoesters of 2,2,4-trimethylpentane-1,3-diols. Such compounds of the formula (I) have to some extent already been commercially available for some time (cf. U.S. Pat. No. 3,329,713) or can be obtained in a known way by esterifying 2,2,4-trimethylpentane-1,3-diol, such as described in Liebigs Ann. 1972, 756, 162-169 or U.S. Pat. No. 3,408,388. Alternative methods for producing the compounds of the formula (I) are, for example, known from U.S. Pat. No. 3,091,632, DE 3403696, U.S. Pat. No. 5,166,413, WO 98/24752 or DE 10207747 and the literature respectively cited therein or can be carried out based on them.

Surprisingly, it has become apparent in our own tests that the alcohols of the formula (I) are capable of influencing the physical properties of chemical preparations (in particular cosmetic and medical preparations) in the above illustrated desired way. Alcohols of the formula (I) stabilise O/W emulsions and in particular O/W emulsions for whose particle size distribution the following applies: D(v, 0.9)=40 μm or less, preferably D(v, 0.9)=30 μm or less. In addition, compounds of the formula (I) consistently increase the viscosity of surfactant-containing preparations (unless specified otherwise below, the viscosity is determined at 22.7° C.).

Furthermore, it has become apparent in our own tests that the preparations according to the invention or the alcohols of the formula (I) contained therein consistently have one, a plurality of or all of the following secondary properties:
easy accessibility,
usability also in concentrated form,
substantial or complete colourlessness,
high stability within the respective preparation
inert behaviour (e.g. with respect to the other constituents of the preparation),
no relevant toxic and/or allergenic effect on humans,
a slight inherent odour.

Preparations according to the invention can additionally, for example, contain additives, such as dipropylene glycol (DPG), diethyl phthalate (DEP), triethyl citrate (TEC), isopropyl myristate (IPM) and benzyl benzoate (BB).

In connection with the present invention, the particle size distribution was determined by means of the principle of laser diffraction. Corresponding equipment for determining the particle size or the particle size distribution is sold by Malvern Instruments GmbH and Malvern Instruments Ltd. Unless specified otherwise below, particle size distributions are determined by means of a device of the Malvern Mastersizer Micro MAF 5000 type. When determining the particle size distribution by means of laser diffraction, the intensity of the scattered light of a laser beam is measured while it penetrates a sample of an O/W emulsion to be tested. From the data obtained, the size of the particles and the associated particle size distribution are calculated from the diffraction pattern produced.

The viscosity of a surfactant-containing (preferably single-phase) preparation according to the invention is dependent on the temperature. Unless specified otherwise below, within the scope of the present invention viscosities of different surfactant-containing preparations are determined at a temperature of 22.7° C., in order to be able to compare them. Unless specified otherwise, within the scope of the present invention the viscosity is determined at the defined temperature by means of a viscosimeter which functions according to the rotation principle. The person skilled in the art uses, for instance, a viscosimeter from Haake (Haake Viscotester 7 plus) for determining the viscosity.

A preparation according to the invention is preferred (as defined above, preferably as defined as preferred above) comprising
one or more alcohols of the formula (I)

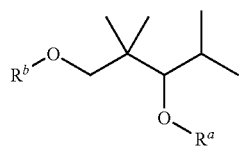

(I)

wherein in each case one of the two moieties $R^a$ or $R^b$ represents hydrogen and the other moiety $R^a$ or $R^b$ in each case represents a straight-chain or branched acyl moiety having 2 to 6 carbon atoms, wherein the preparation is preferably such an O/W emulsion, the particle size distribution for which the following applies: D(v, 0.9)=40 μm or less, and in which the total quantity of these alcohol(s) of the formula (I) having an acyl moiety having 2 to 6 carbon atoms in the preparation is selected in such a way that the O/W emulsion, compared to a comparison emulsion which having an otherwise identical composition does not comprise any such alcohol of the formula (I) having an acyl moiety having 2 to 6 carbon atoms, has an increased emulsion stability, and/or wherein the preparation is preferably such a surfactant-containing preparation (particularly preferably is a single-phase surfactant-containing preparation), in which the total quantity of these alcohol(s) of the formula (I) having an acyl moiety having 2 to 6 carbon atoms in the preparation is selected in such a way that the preparation, compared to a comparison preparation which having an otherwise identical composition does not comprise any such alcohol of the formula (I) having an acyl moiety having 2 to 6 carbon atoms, has an increased viscosity at 22.7° C.

In the above mentioned preferred embodiments of a preparation according to the invention, it therefore decisively comes down to the presence of such alcohols of the formula (I) which have an acyl moiety having two to six carbon atoms. An increased emulsion stability or an increased viscosity (in each case compared to a corresponding comparison preparation) is present, compared to comparison preparations which do not comprise any such alcohol of the formula (I) having an acyl moiety having two to six carbon atoms, independent of the presence of alcohols of the formula (I) having an alkyl moiety having seven to ten carbon atoms. It has become apparent in our own tests that the alcohols of the formula (I) having an acyl moiety having two to six carbon atoms are consistently particularly effective with regard to advantageously setting the above mentioned physical properties.

A preparation according to the invention (as defined above) is particularly preferred, wherein the acyl moiety of one, two, several or all of the alcohols of the formula (I) is selected from the group consisting of acetyl, propionyl, n-butyryl, isobutyryl, crotonyl, n-pentanoyl, isopentanoyl, n-hexanoyl and isohexanoyl, preferably selected from the group consisting of n-butyryl, isobutyryl and crotonyl.

The acyl moieties in the following list also specified as graphic formulas are preferred acyl moieties as moiety $R^b$ or $R^a$ of one, two, several or all (preferably used) alcohols of the formula (I), wherein in the respective structural formula the dashed line represents a covalent bond between the drawn acyl moiety (structural formula) and the adjacent oxygen atom of the alcohol of the formula (I).

| | Formula | Structural formula |
|---|---|---|
| Acetyl | —C(O)—CH₃ | |
| Propionyl | —C(O)—CH₂—CH₃ | |
| n-Butyryl | —C(O)—CH₂—CH₂—CH₃ | |
| Isobutyryl | —C(O)—CH(CH₃)₂ | |

-continued

| Formula | | Structural formula |
|---|---|---|
| Crotonyl | —C(O)—CH=CH—CH$_3$ | |
| n-Pentanoyl | —C(O)—CH$_2$—CH$_2$—CH$_2$—CH$_3$ | |
| Isopentanoyl | —C(O)—CH$_2$—CH(CH$_3$)$_2$ | |
| | —C(O)—CH(CH$_3$)—CH$_2$—CH$_3$ | |
| | —C(O)—C(CH$_3$)$_3$ | |
| n-Hexanoyl | —C(O)—(CH$_2$)$_4$—CH$_3$ | |
| Isohexanoyl | —C(O)—(CH$_2$)$_2$—CH(CH$_3$)$_2$ | |
| | —C(O)—(CH$_2$)—CH(CH$_3$)—CH$_2$—CH$_3$ | |
| | —C(O)—CH(CH$_3$)—(CH$_2$)$_2$—CH$_3$ | |
| | —C(O)—CH(CH$_3$)—CH(CH$_3$)$_2$ | |
| | —C(O)—C(CH$_3$)$_2$—CH$_2$—CH$_3$ | |
| | —C(O)—CH$_2$—C(CH$_3$)$_3$ | |

A preparation according to the invention is often preferred if it comprises a first alcohol of the formula (I) as defined above (in particular as defined as preferred above), wherein the moiety $R^a$ represents hydrogen and the moiety $R^b$ represents a straight-chain or branched acyl moiety (preferably a moiety $R^b$ as listed above).

Correspondingly, a preparation according to the invention preferably comprises a first alcohol of the formula (I) (as defined above, in particular as defined as preferred above, preferably as listed), wherein the moiety $R^a$ represents hydrogen and the moiety $R^b$ represents a straight-chain or branched acyl moiety and optionally additionally a second alcohol of the formula (I) (as defined above, in particular as defined as preferred above) wherein the moiety $R^b$ represents hydrogen and the moiety $R^a$ represents a straight-chain or branched acyl moiety, wherein this acyl moiety $R^a$ of the second alcohol has the same structure as the acyl moiety $R^b$ of the first alcohol, wherein the preparation is preferably an O/W emulsion, the particle size distribution for which the following applies: D(v, 0.9)=40 μm or less, wherein the total quantity of the first alcohol and the second alcohol of the formula (I) in the preparation is preferably selected in such a way that the O/W emulsion, compared to a comparison emulsion which having an otherwise identical composition does not comprise any such first alcohol or second alcohol of the formula (I), has an increased emulsion stability, and/or wherein the total quantity of the first alcohol and the second alcohol of the formula (I) in the (preferably single-phase) preparation is preferably selected in such a way that the preparation, compared to a comparison preparation which having an otherwise identical composition does not comprise any such first alcohol or second alcohol of the formula (I), has an increased viscosity at 22.7° C.

Of course, it is also preferred in this case, i.e. in the case in which the preparation according to the invention comprises a first alcohol of the formula (I) (as defined above, preferably as defined as preferred above), wherein the moiety $R^a$ represents hydrogen and the moiety $R^b$ represents a straight-chain or branched acyl moiety, and comprises a second alcohol, wherein the moiety $R^b$ represents hydrogen and the moiety $R^a$ represents a straight-chain or branched acyl moiety, wherein this acyl moiety $R^a$ of the second alcohol has the same structure as the acyl moiety $R^b$ of the first alcohol, if the respective acyl moiety has two to six carbon atoms (the acyl moiety is again preferably selected from the above list). Again, it is most particularly preferred if the acyl moiety of one, two, several or all of the alcohols of the formula (I), in which the moiety $R^a$ represents hydrogen and the moiety $R^b$ represents a straight-chain or branched acyl moiety, is selected from the group already mentioned above consisting of acetyl, propionyl, n-butyryl, isobutyryl, crotonyl, n-pentanoyl, isopentanoyl, n-hexanoyl and isohexanoyl, preferably selected from the group consisting of n-butyryl, isobutyryl and crotonyl.

According to one aspect of the present invention, preparations according to the invention (as defined above, in particular as defined as preferred above) are preferred, wherein one, two, several or all of the alcohols of the formula (I) (as described above, preferably as defined as preferred above) have a branched acyl moiety.

For some applications, alternatively a preparation according to the invention is preferred, wherein one, two, several or all of the alcohols of the formula (I) (as described above, preferably as defined as preferred above) have an unbranched acyl moiety.

A preparation according to the invention (as defined above, preferably as defined as preferred above) is particularly preferred, wherein the first alcohol of the formula (I) has the formula

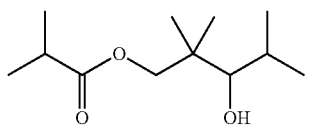

(Ib)

and the optionally present second alcohol of the formula (I) has the formula

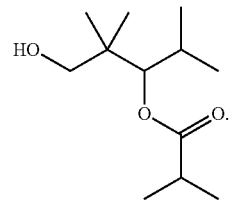

(Ia)

The compound of the formula (Ia) (CAS number 18491-15-1) and the compound of the formula (Ib) (CAS number 77-68-9) are in each case already known per se. Mixtures of compound (Ia) and compound (Ib) are also known (CAS number 25265-77-4). Such mixtures are commercially available, for example from BASF, DSM, Eastman or Perstorp. Yukagaku (1993), 42(1), pages 44-48 discloses the presence of 2-methylpropionic acid-3-hydroxy-2,2,4-trimethylpentylester of the above formula (Ib) in certain plants of the Poly-podiaceae family. The odorous substances hexanal, heptanal, 4-hexen-1-ol, 1-hepten-3-ol, vanillin, cedrol, linalool, beta-ionone, alpha-pinene, isobutyl isobutyrate, alpha-terpineol and ethyl cinnamate were also found. The disclosed mixtures are not a subject matter of the present invention. The disclosed mixtures are not preparations in the sense of the above definition.

Yukagaku (1989), 38(9), pages 689-693, Nippon Nogei Kagaku Kaishi (1989), 63(7), pages 1231-1234 and Nippon Nogei Kagaku Kaishi (1988), 62(12), pages 1763-1768 report on the presence of 2-methylpropionic acid-3-hydroxy-2,2,4-trimethylpentylester of the above formula (1 b) in different types of beans. Inter alia, odorous substances such as, hexanal, 2-phenylethanol, vanillin, maltol, guaiacol, 4-vinylguiacaol, furfuryl alcohol, furfural, cedrol, butyl butyrate and ethyl cinnamate were also identified. The disclosed mixtures are not a subject matter of the present invention. The disclosed mixtures are not preparations in the sense of the above definition.

JP 11222574 describes the use of certain compounds, which are also to be used according to the invention, as a constituent in a water-based sealant for porous building materials. JP 2003171635 describes the use of certain compounds, which are also to be used according to the invention, as a constituent in an adhesive for building materials. However, the present invention does not relate to any of these disclosed compounds and mixtures. The use of the compounds of the formula (1), which are to be used according to the invention, as a constituent of an adhesive or of a sealant for (porous) building materials is, however, generally not preferred within the scope of the present invention, in particular the use as a constituent in a water-based sealant for porous building materials according to JP 11222574 or as a constituent in an adhesive for building materials according to JP 2003171635.

FR 2867972 describes the use of certain compounds, which are to be used according to the invention, in nail varnish. Such a nail varnish is not a subject matter of the present invention. The use in varnishes, particularly in nail varnishes, is generally not preferred within the scope of the present invention. WO 2004/062363 describes the use of 2-methylpropionic acid-3-hydroxy-2,2,4-trimethyl pentyl ester of the above-mentioned formula (Ib) in a mixture for the formation of a biocidal film on a surface. This mixture may optionally contain a perfume oil (fragrance)—not specified there in any more detail. The mixtures described in WO 2004/062363, in particular the mixtures according to Example 1 of WO 2004/062363, are not a subject matter of the present invention. The use of alcohols, to be used according to the invention, of the formula (I), in particular of the formula (Ib), in a mixture for the formation of a biocidal film on a surface, particularly in such a mixture comprising a film-forming agent, is generally not preferred in the context of the present invention.

WO 95/21606 mentions a compound of the formula (I) with $R^b$=isobutyryl and $R^a$=H(3-hydroxy-2,2,4-trimethylpentyl isobutyrate) as a starting material for the production of the unsaturated 2,2,4-trimethylpent-3-en-1-yl-isobutyrate by means of dehydration. In this connection, it is described there that certain 2,2,4-trimethylpenten-1-yl-esters, e.g. the named unsaturated isobutyrate, can be used as odorants and flavourings. The butyrate referred to has a citrusy-fruity, green, floral scent. The mixtures disclosed in WO 95/21606 containing compounds of the formula (I) and uses of compounds of the formula (I) are not a subject matter of the present invention. Mixtures comprising 3-3-hydroxy-2,2,4-trimethylpentyl isobutyrate and 2,2,4-trimethylpent-3-en-1-yl-isobutyrate are generally not preferred in the context of the present invention.

In U.S. Pat. No. 5,942,467, in accordance with an embodiment named there, the substance 2-methylpropionic acid-3-hydroxy-2,2,4-trimethylpentyl ester of the above-mentioned formula (Ib) is proposed as a component of drilling fluids. The present invention does not relate to any use of alcohols, to be used according to the invention, of the formula (I) as a component of drilling fluids, in particular not as a component of drilling fluids in accordance with U.S. Pat. No. 5,942,467. The mixtures disclosed there are not a subject matter of the present invention.

Food Res. Int. 2001, 34, 473-481 and J. Food Science 2002, 67, 848-854 report on the contribution of 2-methylpropionic acid-3-hydroxy-2,2-dimethyl-1-(1-methylethyl)-propyl ester of the above-mentioned formula (Ia) to the flavourings of cooked prawns or cooked octopus. The mixtures disclosed there are not a subject matter of the present invention. In the context of the present invention, a use of alcohols, to be used according to the invention, of the formula (I), in particular of the formula (Ia) in mixtures based on cooked prawns or cooked octopus is not preferred.

The documents cited have not provided any indication to the effect that the alcohols, to be used according to the invention, of the formula (I) are suitable for influencing the important physical parameters of emulsion stability and viscosity.

Preparations according to the invention may comprise odorants. Examples of odorants which may be advantageously used as a component of a preparation according to the invention can be found e.g. in S. Arctander, Perfume and Flavor Chemicals, Vol. I and II, Montclair, N. J., 1969, self-published or H. Surburg, J. Panten, Common Fragrance and Flavor Materials, 5$^{th}$ Ed., Wiley-VCH, Weinheim 2006. In particular, we draw your attention to such odorants as are disclosed in the document EP 2 133 102 A1 already mentioned above. In this context please note in particular paragraphs [0062] and [0063] of said document EP 2 133 102 A1. The odorants named there are particularly advantageous for use in a preferred preparation according to the invention; the odorants named there are, by means of the reference, a component of the present technical disclosure.

The preparations according to the invention (as defined above, preferably as defined above as preferred) may also be ones which in the absence of alcohols of the formula (I) (as defined above) have an unpleasant odour. In such preparations the presence of one or more alcohols of the formula (I) (as defined above) can result in said unpleasant odour being reduced. In such cases, in addition to a reduction in odour already discussed in document EP 2 133 102 A1, the effect of modification or adjustment of physical properties, namely of the emulsion stability and/or the viscosity, that exists in accordance with the present invention, occurs.

Naturally the present invention, however, also relates to such preparations that neither comprise one or more odorants as stated in document EP 2 33 102 A1 nor comprise one or more substances that are responsible for an unpleasant odour as defined by the disclosure in that document.

In accordance with a first aspect of the present invention, the preparation according to the invention is an O/W emulsion. An O/W emulsion according to the invention is thus preferably a preparation according to the invention as defined above (preferably as defined above as preferred). A preferred O/W emulsion according to the invention comprises, as an emulsifying agent, one or more alcohols of the formula (I) as defined above in the discussion of preparations according to the invention, and it has a particle size distribution for which the following applies:

$D(v, 0.9)=40$ μm or less, preferably $D(v, 0.9)=30$ μm or less, $D(v, 0.5)=20$ μm or less, preferably $D(v, 0.5)=15$ μm or less and preferably additionally:

$D(v, 0.1)=2.5$ μm or less, preferably $D(v, 0.1)=2.0$ μm or less.

Therefore particularly preferred in an O/W emulsion according to the invention are particle size distributions of the emulsified oil particles in which a comparatively large number of the particles have a particularly small particle diameter. Such O/W emulsions regularly have a particularly high degree of whiteness.

For O/W emulsions according to the invention, generally what was said above in connection with a preparation according to the invention applies in respect of preferred alcohols of the formula (I). Very particularly preferred is therefore once again the use of an alcohol of the formula (Ib). Preferred O/W emulsions according to the invention comprise, as an emulsifier, one or more alcohols of the formula (I) as defined above in connection with preparations according to the invention (wherein such a preferred O/W emulsion is preferably also a preparation according to the invention as defined above), wherein the stability of the emulsion is set such that after storing this emulsion for 3 weeks (21 days) at 25° C. and a pressure of 1013 HPa under the exclusion of air, the following applies for the particle size distribution: $D(v, 0.9)(t_{21d}):D(v, 0.9)(t_{0d})<2$, preferably <1.5, particularly preferably <1.2 or wherein the instability index of the O/W emulsion, determined by means of a lumisizer from the company LUM, is 75% or less, preferably 65% or less, particularly preferably 55% or less, compared with the instability index of a comparison O/W emulsion, which otherwise having an identical composition does not comprise any alcohol of the formula (I). Concerning the storage, what was said further up applies accordingly; concerning the instability index, determined by means of the lumisizers, what is said further down applies accordingly.

In order to check whether an emulsion has this kind of stability a sample of a corresponding O/W emulsion is stored at 25° C. and at a pressure of 1013 HPa under the exclusion of air for three weeks (21 days). Directly before storage and directly after storage the particle size distribution is determined in each case (for the method for determining the particle size distribution, see above and the examples further down). Then the quotient is formed from the measured values D(v, 0.9) ($t_{21d}$) and D(v, 0.9) ($t_{0d}$). If the quotient is smaller than 2 (preferably <1.5, particularly preferably <1.2) the emulsion investigated has the corresponding stability.

In accordance with a further aspect of the present invention, the preparation according to the invention is a surfactant-containing preparation. A surfactant-containing preparation according to the invention is preferably a preparation according to the invention as has been generally discussed and defined further up. A preferred surfactant-containing (preferably single-phase) preparation according to the invention comprises
    as a means for increasing the viscosity at 22.7° C., one or more alcohols of the formula (I) (as defined above in the discussion of preparations according to the invention),
    one or more anionic surfactants, preferably selected from the group consisting of sulphates and sulphonates, particularly preferably comprising sodium lauryl ether sulphate
    and as appropriate
    one or more further surfactants In respect of preferred alcohols of the formula (I), what was said above concerning the preparations according to the invention once again applies accordingly. Particularly preferred in this respect, therefore, is once again the use of an alcohol of formula (Ib).

Suitable anionic surfactants are for example alkyl sulphates, alkyl ether sulphates, alkyl sulphonates, alkyl aryl sulphonates, alkyl succinates, alkyl sulphosuccinates, N-alkoyl sarcosinates, acyl taurates, acyl isothionates, alkyl phosphates, alkyl ether phosphates, alkyl ether carboxylates, alpha olefin sulphonates, particularly the alkali and alkaline earth metal salts, e. g. sodium, potassium, magnesium, calcium, and also ammonium and triethanolamine salts. The alkyl ether sulphates, alkyl ether phosphates and alkyl ether carboxylates may have between 1 and 10 ethylene oxide or propylene oxide units, preferably 1 to 3 ethylene oxide units, in the molecule.

These include e. g. sodium lauryl sulphate, ammonium lauryl sulphate, sodium lauryl ether sulphate, ammonium lauryl ether sulphate, sodium lauryl sarcosinate, sodium oleyl succinate, ammonium lauryl sulphosuccinate, sodium dodecylbenzene sulphonate, triethanolamine dodecylbenzene sulphonate.

The further surfactants may be non-ionic, amphoteric and cationic surfactants. Examples of suitable non-ionic surfactants are the products of reaction of aliphatic alcohols or alkyl phenols with 6 to 20 C atoms in the alkyl chain, which may be linear or branched, with ethylene oxide and/or propylene oxide. The quantity of alkylene oxide is approx. 6 to 60 moles for one mole of alcohol. Also suitable are, alkylamine oxides, mono- or dialkyl alkanolamides, fatty acid esters of polyethylene glycols, ethoxylated fatty acid amides, alkyl polyglycosides or sorbitan ether esters.

Suitable amphoteric surfactants are e. g. alkyl betaines, alkyl amidopropylbetaines, alkyl sulphobetaines, alkyl glycinates, alkyl carboxyglycinates, alkyl amphoacetates or alkyl amphopropionates, alkyl amphodiacetates or alkyl amphodipropionates.

For example, cocodimethyl sulphopropylbetaine, lauryl betaine, cocamidopropyl betaine or sodium cocamphopropionate may be used.

Quaternary ammonium compounds, for example cetyltrimethylammonium chloride, are suitable cationic surfactants.

Surprisingly, it has been shown in in-house tests that alcohols of the formula (I) (and in particular those alcohols which have already been described above as preferred), regularly bring about a significant increase in the viscosity, in particular in surfactant-containing preparations comprising the surfactant sodium lauryl ether sulphate.

Similar positive results were regularly established in in-house tests for the use of alcohols of the formula (I) in surfactant-containing preparations comprising one or more other anionic surfactants, in particular other anionic surfactants selected from the group consisting of sulphates and sulphonates.

It is clear that an O/W emulsion according to the invention, in the same manner as a surfactant-containing (preferable single-phase) preparation according to the invention, always comprises, alongside the alcohol of the formula (I) or the alcohols of the formula (I) (as defined above, preferably as defined as preferred above), additional compounds.

The person skilled in the art can determine, using few preliminary tests, what total quantity of alcohol of the formula (I) or alcohols of the formula (I) he must choose so that the O/W emulsion according to the invention or the (preferably single-phase) surfactant-containing preparation according to the invention receives the desired physical properties. To this end he will, if necessary, test different total quantities of alcohols of the formula (I) and determine (i) from what total quantity and (ii) up to what total quantity the desired results are achieved. To this end, the person skilled in the art will carry out comparative investigations under analogous conditions.

In order that, in a (preferably single-phase) surfactant-containing preparation according to the invention the one or the more alcohols of the formula (I) (as defined above, preferably as defined as preferred above) can serve as an agent for increasing the viscosity (the comparative increase in the viscosity for surfactant-containing preparations according to the invention was determined at 22.7° C.), they are used in a total quantity suitable for this. With regard to determining, in this respect, a suitable total quantity, the above statements concerning an approach suitable for the person skilled in the art apply accordingly.

The present invention also relates to the use
    (a) of a single alcohol of the formula (I) or
    (b) of a mixture comprising or consisting of two or more different alcohols of the formula (I),

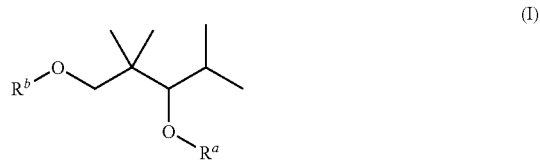

(I)

wherein in each case one of the two moieties $R^a$ or $R^b$ represents hydrogen and the other moiety Ra or $R^b$ in each case represents a straight-chain or branched acyl moiety having 2 to 10 C atoms,
    as the means for modifying one or more physical properties of a formulation (for example a cosmetic or medical or cleaning formulation), wherein the physical properties are selected from the group consisting of emulsion stability and viscosity, preferably as the means for increasing the emulsion stability and/or viscosity of such a formulation.

Concerning preferred alcohols of the formula (I) the above statements on preferred preparations according to the invention, O/W emulsions according to the invention and surfactant-containing preparations according to the invention once again apply accordingly.

Preferred means for modifying the physical property "emulsion stability" are emulsifiers; they stabilise an emulsion.

Concerning the understanding of the terms "emulsion stability" and "viscosity", the above statements once again apply accordingly.

It was surprising and not foreseeable that the alcohols, to be used according to the invention, of the formula (I) (as defined above, preferably as termed preferred above) are capable of influencing the emulsion stability of O/W emulsions and the viscosity of, in particular, surfactant-containing preparations in the way desired by industry, i.e. usually to increase it.

What was said above in connection with preparations according to the invention, in particular concerning preferred acyl moieties, applies accordingly.

Particularly preferred is a use according to the invention as just defined, wherein
in the alternative (a) the one alcohol or
in the alternative (b) one, two or more of the alcohols are alcohols of the formula (I)

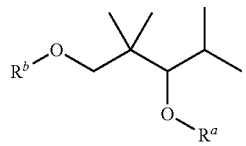
(I)

wherein in each case one of the two moieties $R^a$ or $R^b$ represents hydrogen and the other moiety $R^a$ or $R^b$ in each case represents a straight-chain or branched acyl moiety having 2 to 6 C atoms.

It is also preferred if the acyl moiety of one, two, several or of all of the alcohols of the formula (I) is selected from the group consisting of acetyl, propionyl, n-butyryl, isobutyryl, crotonyl, n-pentanoyl, isopentanoyl, n-hexanoyl and isohexanoyl,
preferably selected from the group consisting of n-butyryl, isobutyryl and crotonyl.

Also preferred is a use according to the invention
of an alcohol of the formula (I) as defined above (preferably as termed preferred above), wherein the moiety $R^a$ represents hydrogen and the moiety $R^b$ represents a straight-chain or branched acyl moiety
or
of a mixture comprising or consisting of
a first alcohol of the formula (I) as defined above (preferably as termed preferred above), wherein the moiety $R^a$ represents hydrogen and the moiety $R^b$ represents a straight-chain or branched acyl moiety and additionally
a second alcohol of the formula (I) as defined above (preferably as termed preferred above).

Also preferred is a use according to the invention (as defined above, preferably as termed preferred above)
of a mixture comprising or consisting of
a first alcohol of the formula (I) as defined above (preferably as termed preferred above), wherein the moiety $R^a$ represents hydrogen and the moiety $R^b$ represents a straight-chain or branched acyl moiety
and
a second alcohol of the formula (I) as defined above (preferably as termed preferred above), wherein the moiety $R^b$ represents hydrogen and the moiety $R^a$ represents a straight-chain or branched acyl moiety,
wherein the moiety $R^a$ of the first alcohol has the meaning of $R^b$ of the second alcohol and the moiety $R^b$ of the first alcohol has the meaning of $R^a$ of the second alcohol.

Very particularly preferred is ultimately a use according to the invention (as defined above, preferably as termed preferred above)
of an alcohol of the formula (Ib)

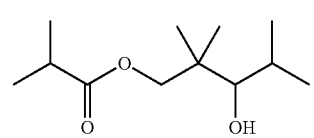
(Ib)

or
of a mixture comprising or consisting of a first and a second alcohol of the formula (I) as defined above (preferably as termed preferred above), wherein the first alcohol of the formula (I) has the formula

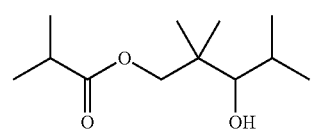
(Ib)

and the second alcohol of the formula (I) preferably has the formula

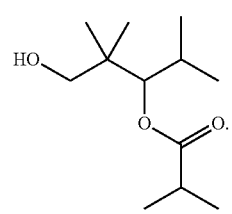
(Ia)

The present invention ultimately also relates to a method
(a) for producing and/or stabilising an O/W emulsion, having the following steps:
mixing two liquids in the presence of a quantity of one, two or more alcohols of the formula (I) acting in an emulsifying manner as defined above (preferably as termed preferred above).

and/or (b) for producing a surfactant-containing preparation with increased viscosity having the following steps:
   mixing a surfactant-containing liquid with a quantity of one, two or more alcohols of the formula (I) as defined above (preferably as termed preferred above) which increases the viscosity.

Preferred therefore, in accordance with a first aspect of the present invention, is a method for producing and/or stabilising an O/W emulsion, having the following steps:
   mixing two liquids in the presence of a quantity of one, two or more alcohols of the formula (I) acting in an emulsifying manner as defined above (preferably as termed preferred above).

Concerning preferred alcohols of the formula (I), the statements made further up in connection with the preparation according to the invention naturally apply once again.

And preferred is therefore, in accordance with a second aspect of the present invention, a method for the production of a surfactant-containing preparation with increased viscosity having the following steps:

mixing a surfactant-containing liquid with a quantity of one, two or more alcohols of the formula (I) as defined above (preferably as termed preferred above) which increases the viscosity.

Concerning the methods according to the invention, what was said above relating to preparations according to the invention, O/W emulsions according to the invention, surfactant-containing preparations according to the invention, and uses according to the invention, applies accordingly.

Below, preferred embodiments of the present invention are explained in more detail with the aid of examples.

EXAMPLES

The following examples show example compositions of preparations according to the invention and described selected properties of such preparations. These properties are, in particular:
- the particle size distribution in O/W emulsions
- the stability of an emulsion
- the viscosity of a surfactant-containing preparation (shampoo).

Preferred embodiments of the present invention will be described in greater detail below using examples.

Examples the following examples show sample compositions of the preparations according to the invention and describe selected features of preparations of this type. These features are in particular:
- the particle size distribution in O/W emulsions
- the stability of an emulsion
- the viscosity of a preparation which contains tensides (shampoo).

Unless otherwise indicated, the amounts indicated in the examples are percentage by weight (w/w %).

1. Particle Size Distribution in O/W Emulsions 1.1 Preparing a Sample

The determination of the particle size distribution was carried out on seven samples with sample numbers 1 to 7 (seven O/W emulsions). The composition of each of these seven samples is shown in Table 1. The components of the formulation were summarised in two groups (phases), A and B. The abbreviation INCI means International Nomenclature of Cosmetic Ingredients, and is based on the individual components of the formulation of the seven samples.

TABLE 1

| | Substance (INCI) | w/w % | | | | | | |
|---|---|---|---|---|---|---|---|---|
| | | 1 | 2 | 3 | 4 | 5 | 6 | 7 |
| A | Potassium Cetyl Phosphate, Hydrogenated Palm Glycerides | 2.0 | 2.0 | 2.0 | 2.0 | 2.0 | 2.0 | 2.0 |
| | Cetearyl Alcohol | 0.7 | 0.7 | 0.7 | 0.7 | 0.7 | 0.7 | 0.7 |
| | Caprylic/Capric Triglyceride | 8.0 | 8.0 | 8.0 | 8.0 | 8.0 | 8.0 | 8.0 |
| | Cetearyl Ethylhexanoate | 4.0 | 4.0 | 4.0 | 4.0 | 4.0 | 4.0 | 4.0 |
| | Dimethicone | 0.1 | 0.1 | 0.1 | 0.1 | 0.1 | 0.1 | 0.1 |
| | 2-Methylpropanoic acid 3-hydroxy-2,2,4-trimethylpentyl ester | — | 0.5 | 1.0 | 2.0 | 3.0 | 4.0 | 5.0 |
| B | Water (Aqua) | 83.7 | 83.2 | 82.7 | 81.7 | 80.7 | 79.7 | 78.7 |
| | Glycerin | 1.5 | 1.5 | 1.5 | 1.5 | 1.5 | 1.5 | 1.5 |
| TOTAL | | 100 | 100 | 100 | 100 | 100 | 100 | 100 |

In a first work step for the manufacture of each sample, the components of the formulation in phase A were prepared in the proportions set out in Table 1, mixed together and heated to a temperature of approx. 80° C. In a second work step, the components of the formulation in phase B were provided accordingly, also mixed together and also heated to approx. 80° C. In a third work step, the heated phase B was added to the heated phase A, mixed with it and emulsified (Ultra Turrax stirrer: 2 minutes, 5000 rpm).

The respective sample was then stirred using a paddle stirrer (150 rpm, 10 minutes) until the sample had cooled to almost room temperature. The pH value of each of the samples was 6.0. This resulted in samples with the sample numbers 1 to 7 listed in Table 1, whereby sample 1 was a reference sample which did not have any link to the formula (I). A first part of each of the prepared samples 1 to 7 was used to determine the particle size distribution. A second part of each of the prepared samples 1 to 7 was used to determine the stability (see 2. further below).

In order to achieve a good comparability of the samples, it was ensures that all of the samples were prepared in an identical manner. From the perspective of the experts carrying out the tests, only the chemical composition of the samples differed; the procedural steps used for the preparation and the procedural parameters set (temperature, stirring conditions etc.) did not differ.

1.2 Determination of the Particle Size Distribution

In order to determine the particle size distribution, in a further work step the relevant parts of samples 1 to 7 were analysed in a master sizer Micro MAF 5000 (manufacturer: Malvern Instruments GmbH). In order to do this, the following sample preparation steps were carried out:

1.3 Results of the Determination of the Particle Size Distribution

The result of the determination of the particle size distribution of the samples with the sample numbers 1 to 7 is shown in Table 2. Three (volume-based) values were determined for each of the seven samples (D(v, 0.1), D(v, 0.5) and D(v, 0.9), whereby

- D(v, 0.1) means that 10% of the particles in the O/W emulsion have a diameter which is smaller than the value indicated in the table
- D(v, 0.5) means that 50% of the particles in the O/W emulsion have a diameter which is smaller than the value indicated in the table
- D(v, 0.9) means that 90% of the particles in the O/W emulsion have a diameter which is smaller than the value indicated in the table

TABLE 2

|   | D (v, 0.1) | D (v, 0.5) | D (v, 0.9) |
|---|---|---|---|
| 1 | 3.47 | 17.44 | 45.84 |
| 2 | 2.43 | 12.62 | 28.93 |
| 3 | 1.97 | 9.92 | 20.02 |
| 4 | 1.67 | 7.91 | 4.48 |
| 5 | 1.49 | 7.07 | 28.93 |
| 6 | 1.49 | 7.82 | 32.29 |
| 7 | 1.64 | 7.97 | 44.20 |

For sample 4 (comprising 2% of an alcohol of formula (I)) for example, a particle size distribution was measured for which the following applies: D(v, 0.5) 7.91 and D(v, 0.9) 4.48. Sample 1 (comprising no alcohol of formula 1) has a particle size distribution for which the following applies: D(v, 0.5) 17.44 and D(v, 0.9) 45.84. Compared to sample 1, therefore, sample 4 has a particle size distribution which comprises a larger amount of smaller particles (in particular based on D(v, 0.5)).

The particle size distribution curve for D(v, 0.5) for samples 1 and 4 are shown as a graph in FIG. 1. In FIG. 1, the continuous curve shows the particle size distribution in sample 1 while the dashed curve shows the particle size distribution in sample 4. The X axis shows the particle diameter in µm. The particle size distribution curve for the particles in sample 4 is clearly shifted towards smaller particles compared to the particle size distribution curve for the particles in sample 1.

2. Stability of an O/W Emulsion

2.1 Preparing a Sample

The determination of the stability of O/W emulsions was carried out on corresponding part of the seven samples with the sample numbers 1 to 7. The composition of these seven samples corresponds to the composition as shown in Table 1. The samples were prepared as described under 1.1.

2.2 Determination of the Stability

The parts of the samples 1 to 7 were analysed using an LUMisizer by the company LUM (LUM GmbH). The lumisizer analyses separation processes (separation of oil and aqueous phase) of several samples simultaneously using centrifugation and the measurement of transmission changes. The parts of the samples are filled into separate cuvettes and centrifuged; in doing this, the profile of the transmission in the longitudinal direction of the cuvettes was continuously determined. The duration of the analysis was 1.25 hours (this corresponds to storage of approximately one month); the analysis was carried out at a rotation speed of 2000 rpm and at a temperature of 25° C. The width of the area of the cuvette in which the aqueous phase is fully separated continuously increased during the analysis period as the centrifugation meant the separation continued. This can be immediately recognised in the transmission profile, see FIG. 3a and FIG. 3b (details in the text below).

2.3. Results of the LUMIsizer Analysis and Determination of the Instability Index It was determined that the seven samples separate to different extents under the conditions according to 2.2. This therefore meant that they had different emulsion stabilities.

Figure 3:
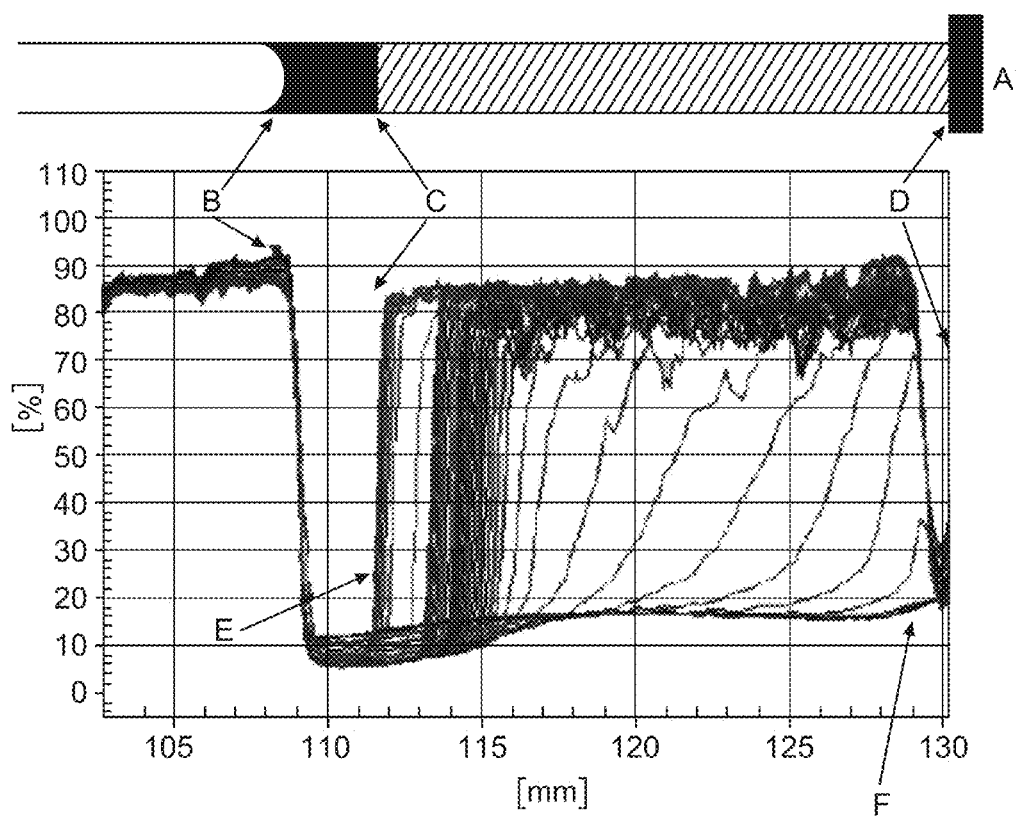
FIG. 3: shows the degree of separation for each of the individual samples 1-7.

The degree of separation of each of the individual samples was determined quantitatively before, during and after treatment according to 2.2 (c.f. FIG. 3; the change in time is shown by the overlapping of individual profiles; one measurement contains 255 individual profiles). In FIG. 3 (X axis: position in mm, Y axis: transmission in %), the labels A, B, C, D, E and F mean the following:

A) analysing cuvette
B) meniscus
C) interface
D) cell bottom
E) last profile
F) first profile At the time t=0, all of the emulsion in each of the individual samples in the cuvette is homogenous; the transmission profile shows that the transmission is equally low in the entire filled area of the cuvette (due to a homogenous distribution of oil particles of low light transmission).

Figure 3A:
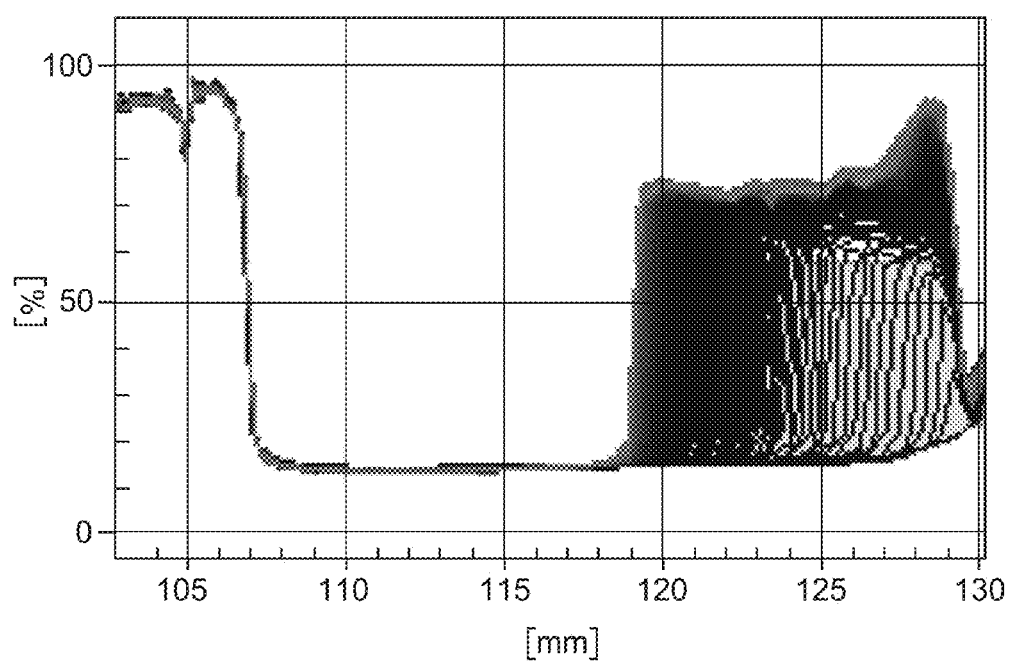
FIG. 3a: shows the transmission profile of sample 1.
Figure 3B:
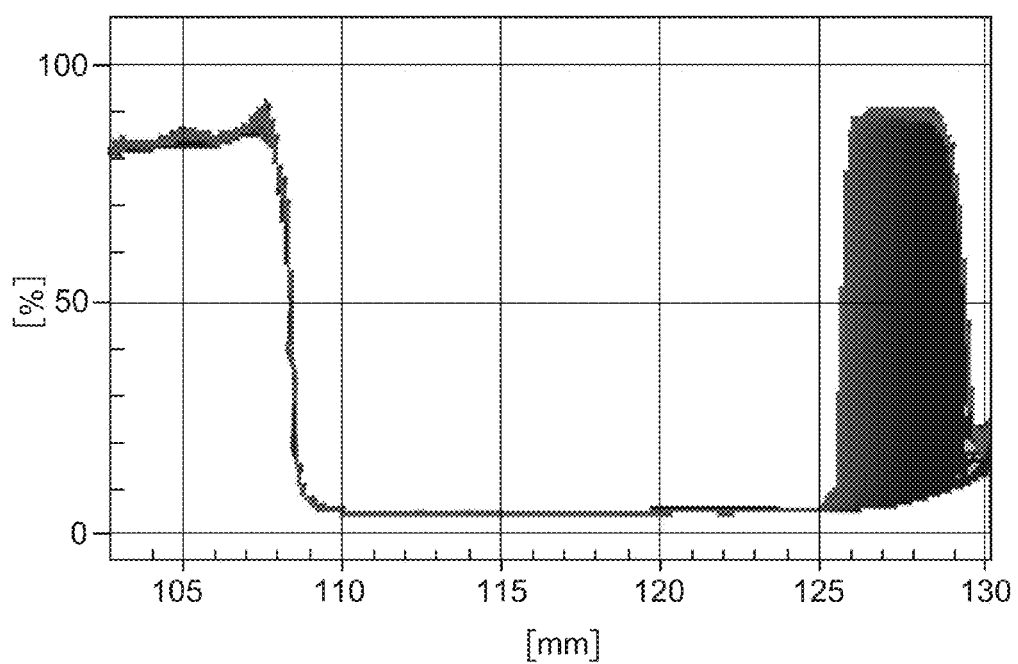
FIG. 3b: shows the transmission profile of sample 4.

As the duration of centrifugation increases, an increasing amount of a fully separated aqueous phase forms; this is shown in the transmission profile by an increasing width of the area with high transmission in the transmission profile (in the transmission profile according to FIG. 3a and FIG. 3b on the right hand side, X axis: position in mm, Y axis: transmission in %) compared to the area in which the oil phase is dispersed or separate (in the transmission profile according to FIG. 3a and FIG. 3b on the left hand side, X axis: position in mm, Y axis: transmission in %).

The width of the separate aqueous phase in the cuvette increases as the duration of centrifugation increases. The width of this area of low light transmission decreases accordingly. This situation is expressed by means of what is known as the instability index. At a given point in time t=0, the instability index of each of the samples is zero (no area of the filled cuvette has high transmission). Over time, the instability index value increases, and the width of the aqueous phase in the cuvette and therefore the width of the area with high transmission in the transmission profile also increases.

Figure 2:
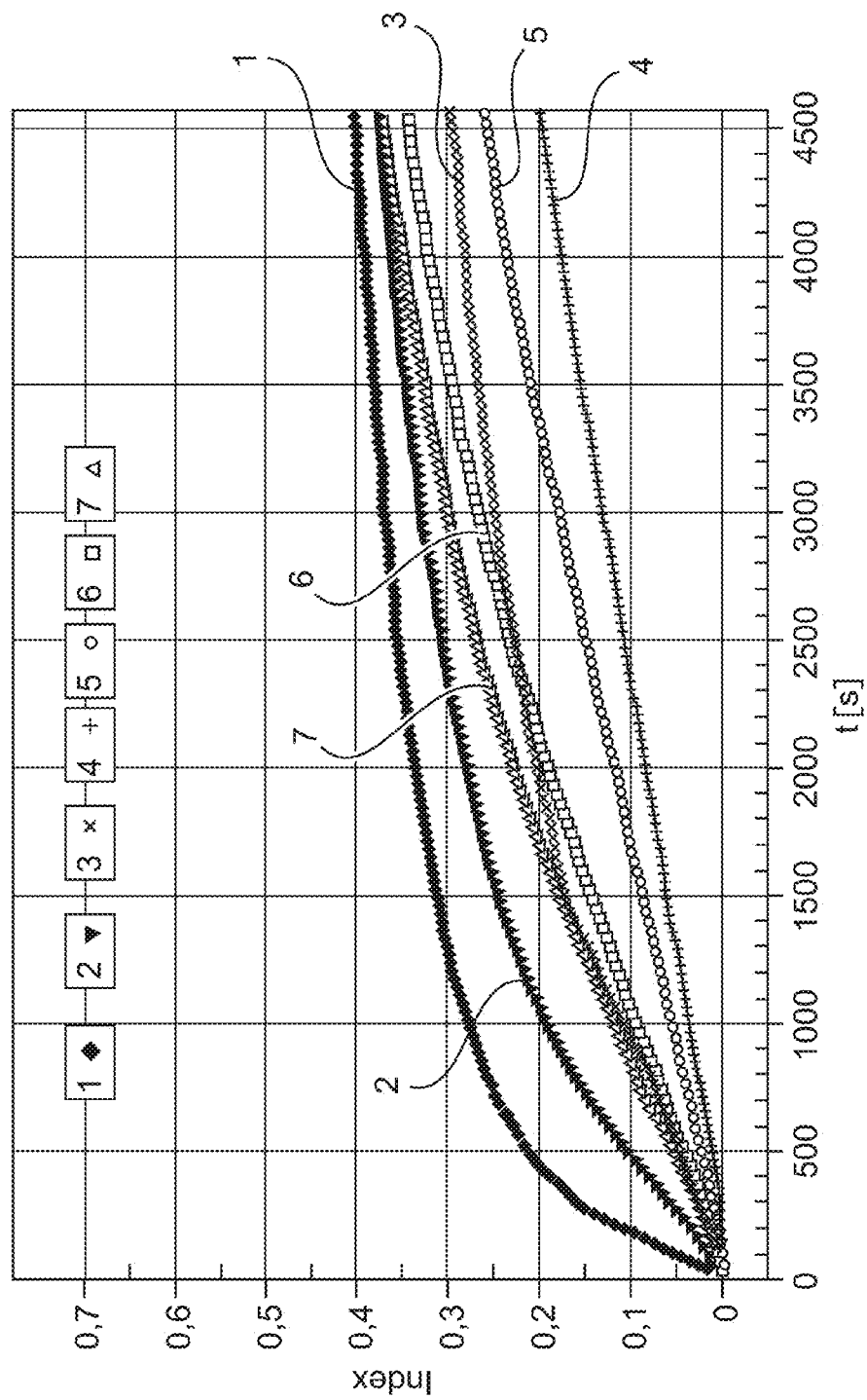
FIG. 2: shows the he instability index (INDEX) of samples 1 to 7.

The instability index (INDEX) of samples 1 to 7 is determined by the LUMIsizer using the duration of centrifugation (1.25 hours=4,500 seconds). The results of the test are shown in FIG. 2, the values for time t=4,500 s (=1.25 h) are shown in Table 3. An INDEX of 0 means very stable, an INDEX of 1 means complete separation.

TABLE 3

|   | INDEX |
|---|---|
| 1 | 0.40 |
| 2 | 0.37 |

TABLE 3-continued

| | INDEX |
|---|---|
| 3 | 0.29 |
| 4 | 0.20 |
| 5 | 0.26 |
| 6 | 0.35 |
| 7 | 0.37 |

Following an analysis lasting 1.25 hours, sample 4 (comprising 2% by weight of an alcohol of formula (I)) achieves an instability index of 0.2, which is the lowest of the samples tested. Sample 4 therefore has the lowest instability over the testing period (the lowest separation of the oil and aqueous phases) and therefore the highest stability in the group of samples 1 to 7.

The instability indices which are determined almost continuously over the entire duration of centrifugation (1.25 hours=4,500 seconds) are shown in FIG. 2 as a graph (as curves). The curve for sample 4 is linear, while the curve for sample 1 experiences exponential saturation even after approximately 1,000 to 1,500 seconds. Sample 4 is therefore not only characterised by a lower instability index (0.2) at the time t=4,500 s (=1.25 h) compared to sample 1 (0.4). The curve progression of sample 4 shows that the separation process in sample 4 not only leads to a lower degree of separation (at time t=4,500 s (=1.25 h)) but also progresses considerably slower (linear curve progression) compared to the separation process in sample 1, which is described by a curve progression with exponential saturation.

FIGS. 3a and 3b show the transmission profile of sample 1 (FIG. 3a) and sample 4 (FIG. 3b).

The transmission profiles in FIGS. 3a and 3b are each the result of 255 (superimposed) individual measurements (individual profiles) which were recorded at equal intervals over the duration of centrifugation of t=4,500 s (=1.25 h).

The transmission profile for sample 1 (comprising no alcohol of the formula (I)) displayed in FIG. 3a shows the (light penetrated) aqueous phase (approx. 70% transmission, on the right hand side in FIG. 3a) in the area from approx. 120 to 130 mm. The area greater than 130 mm corresponds to the base of the cuvette and therefore the cuvette material. In the area from approx. 105 to approx. 120 mm, the oil phase of sample 1 is dispersed or separate (approx. 5% transmission, on the left hand side in FIG. 3a). The area less than 105 mm corresponds to the gas-filled space outside of the sample but within the cuvette.

The transmission profile for sample 4 (comprising 2% by weight of an alcohol of the formula (I)) displayed in FIG. 3b shows the (light penetrated) aqueous phase (approx. 90% transmission, on the right hand side in FIG. 3b) in the area from approx. 125 to 130 mm. In the area from approx. 108 to approx. 125 mm, the oil phase of sample 4 is dispersed or separate (approx. 5% transmission, on the left hand side in FIG. 3b).

The transmission profile for sample 4 (FIG. 3b) therefore shows a less thick (light penetrated) aqueous phase (in the area from approx. 125 to approx. 130 mm) compared to the transmission profile of sample 1 (FIG. 3a, in the area from approx. 120 to approx. 130 mm). Sample 4 therefore has a lower degree of separation than sample 1.

3. Viscosity of a Preparation which Contains Tensides (Shampoo)
3.1 Preparing a Sample The determination of the viscosity is carried out on four samples with sample numbers V1 to V4. The composition of each of these four samples is shown in Table 4. The components of the formulation were summarised in four groups (phases), A and D. The abbreviation INCI means International Nomenclature of Cosmetic Ingredients, and is based on the individual components of the formulation of the four samples.

TABLE 4

| | INCI substance | V1 | V2 | V3 | V4 |
|---|---|---|---|---|---|
| A | Sodium Laureth Sulfate, Lauryl Glycoside | 17.0 | 17.0 | 17.0 | 17.0 |
| | Citric Acid | 0.15 | 0.15 | 0.15 | 0.15 |
| | 1,2 Hexandiol, Caprylyl Glycol | 1.0 | 1.0 | 1.0 | 1.0 |
| | Disodium EDTA | 0.1 | 0.1 | 0.1 | 0.1 |
| | Sodium Chloride | 0.4 | 0.4 | 0.4 | 0.4 |
| B | Water (Aqua) | 76.0 | 75.5 | 75.0 | 74.0 |
| | Polyquaternium-10 | 0.2 | 0.2 | 0.2 | 0.2 |
| C | Potassium Sorbate | 0.15 | 0.15 | 0.15 | 0.15 |
| D | Cocoamidoproyl Betaine | 5.0 | 5.0 | 5.0 | 5.0 |
| | Trimethyl Hydroxypentyl Isobutyrate | — | 0.5 | 1.0 | 2.0 |
| | TOTAL | 100.0 | 100.0 | 100.0 | 100.0 |

In a first work step, the components of the formulation in phase A were prepared and carefully stirred together until the initial formation of foam is observed (the stirring process was stopped as soon as the first formation of foam was observed). In a second work step, the polyquaternium-10 (Ucare Polymer JR-400) was provided, mixed with the water and the mixture was heated to approx. 50° C., so the polymer started to swell up. The swelling process as ended as soon as the dispersion became clear and slight viscosity was observed. In a third work step, the components of the formulation of phases B, C and D were added with continuous stirring of phase A. The pH of the resulting mixtures were then set to approx. 5.4 to 5.8. This resulted in samples V1 to V4.

3.2 Determination of the Viscosity

The viscosity of samples V1 to V4 were determined at a temperature of 22.7° C. using a rotation viscometer (HAAKE Viscotester 7 with a type 3 shaft).

3.3. Results of the Determination of Viscosity

The result of the determination of viscosity of the samples with the sample numbers V1 to V4 is shown in Table 5.

TABLE 5

| | V1 | V2 | V3 | V4 |
|---|---|---|---|---|
| [mPas] | 480 | 1240 | 1324 | 566 |

Sample V3 (comprising 1% by weight of an alcohol of the formula (I)) showed the highest viscosity compared to the other samples (1324 mPas). Sample V1 (comprising no alcohol of the formula (I)) had a viscosity of 480 mPas and therefore had a significantly reduced viscosity compared to sample V3.

4. Further Example Formulations
4.1 Shower Gel/Shampoo

| Starting material | INCI substance | w/w % |
|---|---|---|
| Water, demin. | Water (Aqua) | 76.7 |
| Plantacare PS 10 | Sodium Laureth Sulfate, Lauryl Glucoside | 20.0 |
| SymDiol 68, 108580 | Hexylene Glycol, Caprylyl Glycol | 1.0 |
| EDTA BD | Disodium EDTA | 0.1 |

-continued

| Starting material | INCI substance | w/w % |
|---|---|---|
| Sodium Chloride | Sodium Chloride | 1.0 |
| Citric Acid, cryst. | Citric Acid | 0.2 |
| Alcohol of the formula (I) | Trimethyl Hydroxypentyl Isobutyrate | 1.0 |

4.2 Standard O/W Emulsion

| Starting material | INCI substance | w/w % |
|---|---|---|
| Emulsiphos | Potassium Cetyl Phosphate, Hydrogenated Palm Glycerides | 2.0 |
| Cutina PES | Pentaerythrityl Distearate | 2.0 |
| PCL Solid | Stearyl Heptanoate, Stearyl Caprylate | 2.0 |
| Lanette O | Cetearyl Alcohol | 2.5 |
| PCL Liquid 100 | Cetearyl Ethylhexanoate | 5.0 |
| Isodragol | Triisononanoin | 2.0 |
| Dow Corning 246 Fluid | Cyclohexasiloxane, Cyclopentasiloxane | 2.0 |
| Dragoxat 89 | Ethylhexyl Isononanoate | 3.0 |
| Ultrez-10 | Carbomer | 0.2 |
| Water | Water (Aqua) | 74.1 |
| Alcohol of the formula (I) | Trimethyl Hydroxypentyl Isobutyrate | 5.0 |
| Sodium Hydroxide 10% sol. | Sodium Hydroxide | 0.2 |
| TOTAL | | 100 |
| pH | | 6.0 |

The invention claimed is:

1. A surfactant-containing preparation comprising:
one or more alcohols of the formula (I),

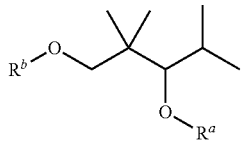

(I)

wherein in each case one of the two moieties $R^a$ or $R^b$ represents hydrogen and the other moiety $R^a$ or $R^b$ in each case represents a straight-chain or branched acyl moiety having 2 to 10 carbon atoms; and
one or more anionic surfactants;
wherein the preparation is an O/W emulsion, the particle size distribution for which the following applies: D(v, 0.9)=40 μm or less, and
wherein the total quantity of the alcohol(s) of the formula (I) in the preparation is selected in such a way that the preparation, compared to a comparison preparation which having an otherwise identical composition does not comprise any alcohol of the formula (I), has an increased viscosity at 22.7° C.

2. The surfactant-containing preparation according to claim 1, wherein one of the two moieties $R^a$ or $R^b$ represents hydrogen and the other moiety $R^a$ or $R^b$ in each case represents a straight-chain or branched acyl moiety having 2 to 6 carbon atoms.

3. The surfactant-containing preparation according to claim 1, wherein the acyl moiety is selected from the group consisting of acetyl, propionyl, n-butyryl, isobutyryl, crotonyl, n-pentanoyl, isopentanoyl, n-hexanoyl and isohexanoyl.

4. The surfactant-containing preparation according to claim 1, wherein the moiety $R^a$ represents hydrogen and the moiety $R^b$ represents a straight-chain or branched acyl moiety.

5. The surfactant-containing preparation according to claim 4 comprising an alcohol of the formula (I) having the formula

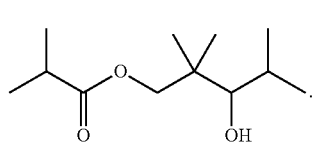

(Ib)

6. The surfactant-containing preparation of claim 1, having a particle size distribution for which the following applies:
D(v, 0.9)=40 μm or less,
D(v, 0.5)=20 μm or less,
D(v, 0.1)=2.5 μm or less.

7. The surfactant-containing preparation of claim 1 comprising as an emulsifying agent one or more alcohols of formula (I), wherein the stability of the emulsion is set in such a way that after storing the preparation for 3 weeks (21 days) at 25° C. and at a pressure of 1013 HPa hermetically sealed, the following applies for the particle size distribution: D(v, 0.9) ($t_{21d}$):D(v, 0.9) ($t_{0d}$)<2, or wherein the instability index of the O/W emulsion is 75% or less, compared to the instability index of a comparison O/W emulsion which otherwise having an identical composition does not comprise any alcohol of the formula (I).

8. The surfactant-containing preparation according to claim 4 comprising a second alcohol of formula (I), wherein the moiety $R^b$ represents hydrogen and the moiety $R^a$ represents a straight-chain or branched acyl moiety, wherein this acyl moiety $R^a$ of the second alcohol has the same structure as the acyl moiety $R^b$ of the first alcohol.

9. The surfactant-containing preparation according to claim 5 comprising a second alcohol of the formula (I) having the formula

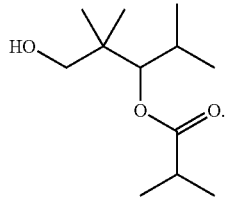

10. The surfactant-containing preparation of claim 1 comprising as an emulsifying agent one or more alcohols of formula (I), wherein the stability of the emulsion is set in such a way that after storing the preparation for 3 weeks (21 days) at 25° C. and at a pressure of 1013 HPa hermetically sealed, the following applies for the particle size distribution: D(v, 0.9) ($t_{21d}$):D(v, 0.9) ($t_{0d}$)<1.5.

11. The surfactant-containing preparation of claim 1 comprising as an emulsifying agent one or more alcohols of formula (I), wherein the instability index of the O/W emulsion is 55% or less, compared to the instability index of a comparison O/W emulsion which otherwise having an identical composition does not comprise any alcohol of the formula (I).

12. The surfactant-containing preparation according to claim 1, wherein one or more anionic surfactants are selected from the group consisting of sulphates and sulphonates.

13. The surfactant-containing preparation according to claim 12, wherein one or more anionic surfactants comprises sodium lauryl ether sulphate.

14. A method
for producing a surfactant-containing preparation of claim 1 comprising
mixing an anionic surfactant-containing liquid with a quantity of one, two or more alcohols of formula (I),

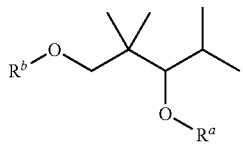
(I)

wherein in each case one of the two moieties $R^a$ or $R^b$ represents hydrogen and the other moiety $R^a$ or $R^b$ in each case represents a straight-chain or branched acyl moiety having 2 to 10 carbon atoms.

15. A method for increasing stability and/or viscosity of an emulsion comprising including in the emulsion one or more anionic surfactants and:
(a) a single alcohol of formula (I) or
(b) a mixture of two or more different alcohols of formula (I),

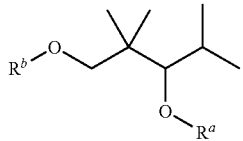
(I)

wherein in each case one of the two moieties $R^a$ or $R^b$ represents hydrogen and the other moiety $R^a$ or $R^b$ in each case represents a straight-chain or branched acyl moiety having 2 to 10 carbon atoms.

16. The method according to claim 15, wherein in each case one of the two moieties $R^a$ or $R^b$ represents hydrogen and the other moiety $R^a$ or $R^b$ in each case represents a straight-chain or branched acyl moiety having 2 to 6 carbon atoms.

17. The method according to claim 16, wherein the acyl moiety is selected from the group consisting of acetyl, propionyl, n-butyryl, isobutyryl, crotonyl, n-pentanoyl, isopentanoyl, n-hexanoyl and isohexanoyl.

18. The method according to claim 15 comprising including in the emulsion an alcohol of formula (Ib)

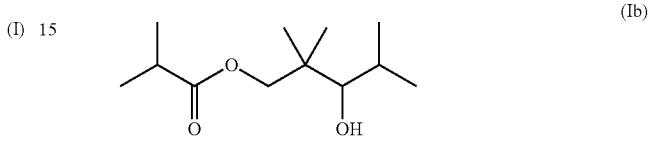
(Ib)

or of a mixture comprising a first alcohol and a second alcohol of the formula (I), wherein the first alcohol of formula (I) has the formula

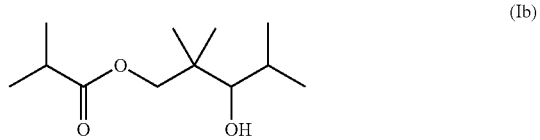
(Ib)

and the second alcohol of formula (I) has the formula

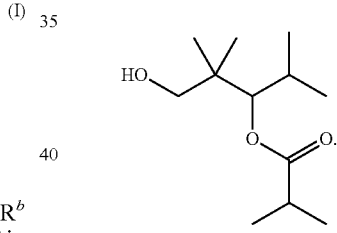

* * * * *